United States Patent
Troxel et al.

(10) Patent No.: US 9,775,853 B2
(45) Date of Patent: Oct. 3, 2017

(54) HEMOSTATIC COMPOSITIONS AND METHODS

(71) Applicant: Biomet Manufacturing, LLC, Warsaw, IN (US)

(72) Inventors: Karen S. Troxel, Warsaw, IN (US); Michael Ponticiello, Mission Viejo, CA (US)

(73) Assignee: Biomet Manufacturing, LLC., Warsaw, IN (US)

( * ) Notice: Subject to any disclaimer, the term of this patent is extended or adjusted under 35 U.S.C. 154(b) by 39 days.

(21) Appl. No.: 14/209,887

(22) Filed: Mar. 13, 2014

(65) Prior Publication Data

US 2014/0274875 A1    Sep. 18, 2014

Related U.S. Application Data

(60) Provisional application No. 61/800,317, filed on Mar. 15, 2013.

(51) Int. Cl.

| | | |
|---|---|---|
| *A01N 37/18* | (2006.01) | |
| *A61K 38/00* | (2006.01) | |
| *A61P 31/00* | (2006.01) | |
| *A01N 57/26* | (2006.01) | |
| *A61K 31/685* | (2006.01) | |
| *A23J 7/00* | (2006.01) | |
| *A61K 45/06* | (2006.01) | |
| *A61L 24/00* | (2006.01) | |

(52) U.S. Cl.
CPC ............ *A61K 31/685* (2013.01); *A61K 45/06* (2013.01); *A61L 24/0005* (2013.01); *A61L 24/0015* (2013.01); *A61L 24/0042* (2013.01); *A61L 2300/22* (2013.01); *A61L 2300/404* (2013.01); *A61L 2400/04* (2013.01)

(58) Field of Classification Search
USPC ........................................................ 514/16.7
See application file for complete search history.

(56) References Cited

U.S. PATENT DOCUMENTS

| | | |
|---|---|---|
| 2,615,447 A | 10/1952 | Cohen |
| 4,721,618 A | 1/1988 | Giles et al. |
| 4,749,585 A | 6/1988 | Greco et al. |
| 5,169,645 A | 12/1992 | Shukla et al. |
| 5,660,854 A | 8/1997 | Haynes et al. |
| 5,755,788 A | 5/1998 | Strauss |
| 5,798,117 A | 8/1998 | New et al. |
| 5,972,366 A | 10/1999 | Haynes et al. |
| 6,165,487 A | 12/2000 | Ashkar et al. |
| 6,420,454 B1 | 7/2002 | Wenz et al. |
| 6,599,517 B1 | 7/2003 | Ljusberg-Wahren et al. |
| 6,863,693 B2 | 3/2005 | Lloyd et al. |
| 6,998,134 B2 | 2/2006 | Schmidmaier et al. |
| 7,015,193 B2 | 3/2006 | Butenas et al. |
| 7,074,425 B2 | 7/2006 | Constantine et al. |
| 7,163,691 B2 | 1/2007 | Knaack et al. |
| 7,357,947 B2 | 4/2008 | Nimni |
| 7,413,806 B2 | 8/2008 | Ong et al. |
| 7,955,616 B2 | 6/2011 | Kronenthal |
| 7,989,000 B2 | 8/2011 | Kronenthal |
| 8,092,824 B2 | 1/2012 | Kuhn et al. |
| 2001/0003599 A1 | 6/2001 | Chinn et al. |
| 2003/0049326 A1 | 3/2003 | Nimni |
| 2003/0050225 A1* | 3/2003 | Butenas ............... A61K 9/127 514/13.5 |
| 2006/0002976 A1 | 1/2006 | Kronenthal |
| 2006/0013857 A1 | 1/2006 | Kronenthal |
| 2006/0225195 A1 | 10/2006 | Scholer |
| 2007/0053957 A1 | 3/2007 | Kennedy et al. |
| 2007/0178158 A1 | 8/2007 | Knaack et al. |
| 2008/0063671 A1 | 3/2008 | Morris et al. |
| 2009/0137663 A1 | 5/2009 | Denney et al. |
| 2010/0209475 A1 | 8/2010 | Kumar |
| 2011/0038910 A1 | 2/2011 | Faucher et al. |
| 2012/0058150 A1 | 3/2012 | Prawel et al. |
| 2012/0082706 A1 | 4/2012 | Nakagawa et al. |
| 2012/0093565 A1 | 4/2012 | Drew |
| 2012/0258159 A1 | 10/2012 | Vogt |
| 2013/0101673 A1* | 4/2013 | Borden ........................ 424/492 |
| 2013/0288951 A1* | 10/2013 | Troxel .................... A61L 27/28 514/2.3 |
| 2014/0275287 A1* | 9/2014 | Knaack et al. ............... 514/769 |

FOREIGN PATENT DOCUMENTS

| | | |
|---|---|---|
| CN | 101011598 A | 8/2007 |
| EP | 0479582 A1 | 4/1992 |
| EP | 2351556 A2 | 8/2011 |
| GB | 2135878 A | 9/1984 |
| JP | 3294221 B2 | 6/2002 |
| JP | 2007106679 A | 4/2007 |
| JP | 2014005219 A | 1/2014 |
| WO | 9321970 A1 | 11/1993 |
| WO | 9616643 A1 | 6/1996 |
| WO | 9907811 A1 | 2/1999 |
| WO | 9947187 A1 | 9/1999 |
| WO | 03053218 A2 | 7/2003 |
| WO | 2007097887 A2 | 8/2007 |
| WO | 2011007353 A1 | 1/2011 |
| WO | 2011089624 A2 | 7/2011 |
| WO | 2012029971 A1 | 3/2012 |
| WO | 2012142317 A1 | 10/2012 |
| WO | 2013163577 A1 | 10/2013 |

OTHER PUBLICATIONS

Anonymous. "Phospholipon 90G" Product Description Page. Phospholipid GmbH. Mar. 2007.*

(Continued)

*Primary Examiner* — Christina Bradley
*Assistant Examiner* — Zachary J Miknis
(74) *Attorney, Agent, or Firm* — Schwegman Lundberg & Woessner, P.A.

(57) ABSTRACT

Compositions and methods for achieving hemostasis. Hemostatic compositions comprise a phospholipid, and optionally, an anti-infective agent. The hemostatic composition can be administered to a bleeding bone to achieve hemostasis.

18 Claims, 1 Drawing Sheet

(56) References Cited

OTHER PUBLICATIONS

Mapara et al. "Rabbit as an animal model for experimental research" Dent. Res. J. 9:111-118. Published Mar. 2012.*
Wellisz T "Management of Bone Bleeding During Surgery and its Impact on the Incidence of Post-Operative Osteomyelitis" p. 153-180 in Osteomyletis. Edited by M. Baptista. Published Mar. 23, 2012.*
ProductInformation for 1,2-Diacyl-sn-glycero-3-phosphocholine, Sigma-Adrich.*
Product Information of Phospholipon 90H, Phospholipid GmbH. 2007.*
Bosetti, M. "Cell Behaviour on Phospholipids-Coated Surfaces" Journal of Materials Science: Materials in Medicine (2007), 18(4), 611-617.
ISO Intramuscular Implantation Test, ISO 10993-6, "Tests for Local Effects after Implantation" (2007).
Malheiros, "Development and Characterization of Phosphatidylcholine Nanovesicles Containing the Antimicrobial Peptide Nisin" Food Research International. 43:1198-1203, May 2010.
Matl, F.D. "New Anti-Infective Coatings of Medical Implants" Antimicrobial Agents and Chemotherapy, p. 1957-1963. Jun. 2008.
McHugh, S.M. "The Role of Topical Antibiotics Used as Prophylaxis in Surgical Site Infection Prevention" J. Antimicrobial Chemotherapy 66:693-701 (2011).
Mikhalovsky, S. V. "Current Trends in Biomaterial Coatings" NATO Science Series, II: Mathematics, Physics and Chemistry (2003), 102 (Nanostructured Materials and Coatings in Biomedical and Sensor Applications), 15-26.
Paul, W. "Antibiotic Loaded Hydroxyapatite Osteoconductive Implant Material—In Vitro Release Studies" Journal of Materials Science Letters (1995), 14(24), 1792-4.
Prawel, D. A. "Novel Electro-Spray Technique for Applying Phospholipid Coatings to Titanium" Transactions of the Annual Meeting of the Society for Biomaterials (2010), 32.
Price, J.S. "Controlled Release of Antibiotics from Coated Orthopedic Implants" Journal of Biomedical Materials Research, vol. 30, 281-286 (1996).
Willumeit, R. "Phospholipids as Implant Coatings" J Mater Sci: Mater Med 18:367-380 (2007).
"European Application Serial No. 14159968.8, Extended European Search Report dated Jun. 27, 2014", 8 pgs.
"European Application Serial No. 14159968.8, Response filed Mar. 17, 2015 to Extended European Search Report dated Jun. 17, 2014", 11 pgs.

\* cited by examiner

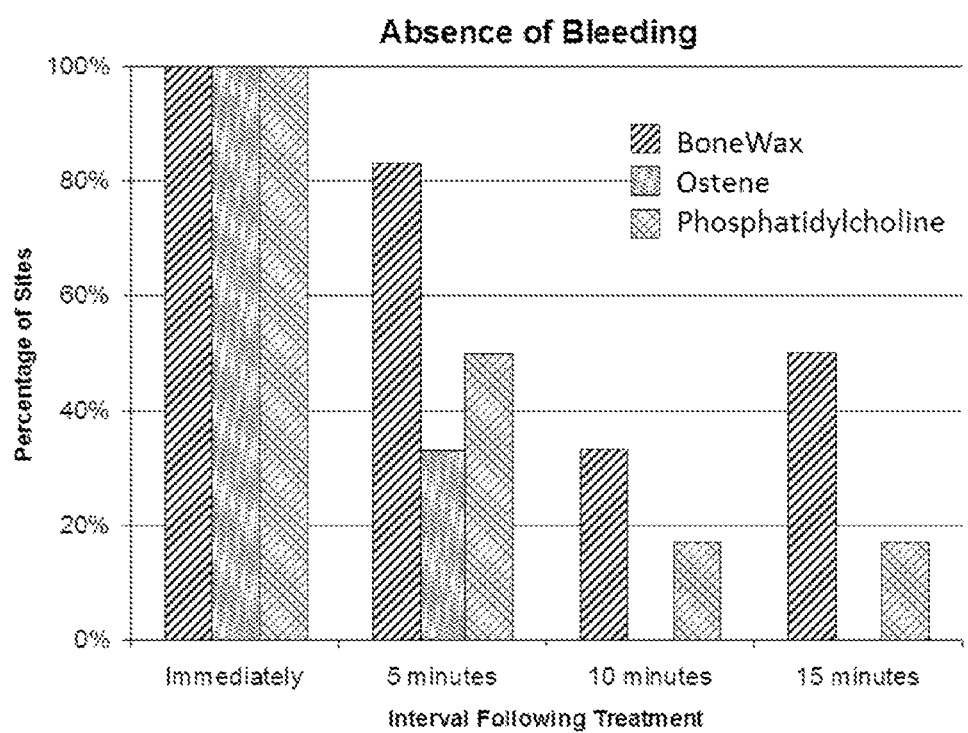

HEMOSTATIC COMPOSITIONS AND METHODS

CROSS-REFERENCE TO RELATED APPLICATIONS

This application claims the benefit of U.S. Provisional Application No. 61/800,317, filed on Mar. 15, 2013. The entire disclosure of the above application is incorporated herein by reference.

INTRODUCTION

Bone is highly vascularized and, when cut, can bleed profusely. Bleeding can be difficult to control during orthopedic surgeries, particularly involving the spine and sternum. Moreover, techniques such as cauterization that can be used to control bleeding in soft tissue are not effective in bone. Instead, hemostasis can be achieved in bleeding bone by mechanical tamponade of a putty or waxy like substance to fill pores of the bone, especially in cancellous bone, thus preventing the blood from continuing to flow out of the bone.

The standard material used for achieving bone hemostasis is comprised of beeswax, paraffin, and isopropyl palmitate (BoneWax). However, while BoneWax is very effective at stopping bleeding, it is not metabolized and remains as a foreign object in the body. Because it does not degrade, BoneWax can interfere with bone repair. For example, a sternotomy is a procedure in which bone is cut and the cut surfaces are reapposed and wired together to encourage the cut surfaces to reattach to each other. When BoneWax is used in a sternotomy to stop bone bleeding, the BoneWax remains in the body permanently. Another problem that arises from using a permanent material for bone hemostasis is that, like all foreign bodies, it can actually serve as a locus for infection.

Several resorbable or biodegradable formulations have been developed for bone hemostatic agents. For instance, U.S. Pat. No. 6,420,454, Wenz et al., issued Jul. 16, 2002, describes a polyester oligomer, synthesized from polyol, lactide, and glycolide, that is mixed with water-soluble polymers such as polyethyleneglycols. U.S. Pat. No. 7,955,616, Kronenthal, issued Jun. 7, 2011, describes a bone hemostasis putty comprising finely powdered carboxylic acid salt, a pyrollidone, and a dispersing vehicle that is necessary to convert the carboxylic acid salt into a form of a putty. U.S. Pat. No. 7,074,425, Constantine et al., issued Jul. 11, 2006, describes a bone hemostatic putty formulation comprised of different sizes of polyethylene glycols. U.S. Patent Application Publication No. 2012/0258159, Vogt, published Oct. 11, 2012, describes a bone hemostatic agent comprised of a mixture of saturated triglycerides, a filling agent that is a particulate, and a third compound with a melting temperature below 37° C.

Unfortunately, the number of synthesis and compounding steps makes all of these formulations more expensive to produce than beeswax products, which are quite inexpensive. Therefore, there is still a need for a resorbable, biodegradable, and biocompatible bone hemostatic agent that functions well as a mechanical tamponade, but which could be produced at a low cost so as to be commercially competitive with beeswax-based products.

SUMMARY

The present technology provides phospholipid compositions capable of achieving hemostasis in bleeding bone. In various embodiments, the phospholipid is phosphatidylcholine. Optionally, the phospholipid compositions can comprise at least one anti-infective agent.

The present technology also provides methods for achieving hemostasis in bleeding bone. The method comprises administering a safe and effective amount of phospholipid composition to a site of bone bleeding. Administering can be performed by mechanical tamponade. In various embodiments, the phospholipid composition can comprise at least one anti-infective agent. Preferably, the phospholipid is phosphatidylcholine.

DRAWINGS

FIG. 1 shows a graph depicting the percentage of defect sites not bleeding at five minute intervals following treatment.

It should be noted that the FIGURE set forth herein is intended to exemplify the general characteristics of materials and methods among those of the present technology, for the purpose of the description of certain embodiments. This FIGURE may not precisely reflect the characteristics of any given embodiment, and is not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology provides hemostatic phospholipid compositions. The phospholipid compositions have a malleable, putty-like consistency similar to wax, but are biocompatible, resorbable, and biodegradable. As normal components of a body's tissues, phospholipids do not present any unusual or un-natural degradation products, such as the acids produced by hydrolysis of lactide- and glycolide-resorbable polymers. Optionally, the phospholipid compositions can have one or more anti-infective agents that confer broad spectrum antimicrobial activity against bacteria and yeast and other fungal organisms. The phospholipid compositions can stop a bone defect from bleeding in a mammalian subject, and the optional anti-infective activity prevents or confers resistance to the growth of bacteria or fungi that may be present at the site of the defect.

Phospholipids are a major constituent of cell membranes, thus are naturally-occurring in the body. Phospholipids are amphipathic molecules that are characterized by a hydrophilic head, which consists of a polar group, a phosphate and glycerol, and two hydrophobic fatty acid tails, which may be saturated or unsaturated. The fatty acids that may be short-chain fatty acids with fewer than 6 carbons, medium-chain fatty acids with 6-12 carbons, long-chain fatty acids with more than 12 carbons or very long-chain fatty acids with more than 22 carbons. In various embodiments, the fatty acid tails are either 16 or 18 carbons long, wherein the 18-carbon chains are predominantly unsaturated. Examples of saturated fatty acids include propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacoylic acid, cerotic acid, heptacosylic acid, montanic acid, nonacosylic acid, melissic acid, nenatriacontylic acid, lacceroic acid, psyllic acid, geddic acid, ceroplastic acid and hexatriacontylic acid. Examples of unsaturated fatty acids include myristoleic acid, palmitoleic acid, sapienic acid, oleic acid, elaidic acid, vaccenic acid, linoleic acid, linoelaidic acid, α-linolenic acid, arachindonic acid, eicosapentaenoic acid, erucic acid and docosahexaenoic acid. Furthermore, the unsaturated fatty acids may be polyunsaturated. The fatty acids of the phospholipid may be saturated, unsaturated, polyunsaturated or combinations thereof.

In some embodiments, the phospholipid is lecithin. Lecithin is a yellow-brownish fatty mixture comprising phospholipids (phosphatidylcholine, phoshpatidylethanolamine and phosphatidylinositol), fatty acids, glycerol, glycolipids, carbohydrates, sphingolipids and triglycerides. The primary phospholipid components of lecithin are 13-18% phosphatidylcholine, 10-15% phoshatidylethanolamine, 10-15% phosphatidylinositol, and 5-12% phosphatidic acid. Lecithin is isolated from plant (such as soy bean) and animal tissues and from egg yolk. Lecithin can easily be extracted chemically (with hexane) or mechanically from readily available sources, such as soy beans. It has low solubility in water. In aqueous solution, the phospholipids in lecithin can form liposomes, bilayer sheets, micelles, or lamellar structures, depending on hydration and temperature. These solutions result in a type of surfactant that is usually classified as amphipathic. Lecithin is sold as a food supplement and for medical uses. In cooking, it can be used as an emulsifier and to prevent sticking, for example in non-stick cooking spray. Commercially available liquid lecithin useful herein includes Phosal® 53 MCT, available from Lipoid, (Koln, Germany) which comprises at least about 53% phosphatidylcholine, up to 6% lysophosphatidylcholine and from 3% to 6% ethanol.

Phosphatidylcholine is a preferred phospholipid. Phosphatidylcholine is characterized by a polar choline group at the head of the phospholipid and two hydrophobic fatty acid tails. Phosphatidylcholine can be prepared from lecithin. Such a preparation is commercially available from the American Lecithin Company (Oxford, Conn.) as Phospholipon® 90G and comprises at least 94% phosphatidylcholine, up to 4.0% lysophosphatidylcholine and up to 0.3% tocopherol. Phospholipon® 90G is also commercially available from Lipoid (Koln, Germany). Phosphatidyl choline purified from natural sources, such as egg and soy, are commercialized by Avanti Polar Lipids, Inc. (Alabaster, Ala.).

Synthetic phosphatidylcholines are also available from several sources and with different lengths of fatty acid chains and different degrees of saturation. These are readily available commercially and are typically used in drug delivery formulations. Also, naturally derived purified phosphatidylcholine can be hydrogenated to fully saturate the fatty acid chains, producing a solid that is a white powder and no longer has a waxy consistency. The hydrogenated phosphatidylcholine and the synthetic phosphatidylcholines can be combined to create compositions with differing consistencies. For instance, hydrogenated phosphatidylcholine can be added to natural unsaturated phosphatidylcholine in order to increase the stiffness of the composition. If an additive such as an anti-infective agent needs to be pre-mixed with a liquid lipid mixture such as Phosal 53MCT (Lipoid, Koln, Germany) prior to addition to the phospholipid in order to utilize a mechanical mixing process, then a stiffer lipid such as a fully saturated (hydrogenated) phosphatidylcholine might be added to the formulation in order to counteract the softening effects of the liquid lipid component.

For bone hemostatic applications, purified soy derived phosphatidylcholine is an ideal phospholipid because it dissolves readily, will not interfere with biologic fixation, and is biocompatible and compatible with bone repair. The amphipathic nature and the unsaturated fatty acid components allow the phosphatidylcholine to disperse rapidly in aqueous environments such as in vivo. In contrast, fully saturated triacylglycerols and saturated fatty acids are not soluble in water, resulting in a hindrance to dispersion in vivo. Purified phosphatidylcholine requires no other component or additives to achieve properties required for a bone hemostatic agent.

As mentioned above, hemostatic phospholipid compositions can comprise one or more anti-infective agents that confer broad spectrum antimicrobial activity against bacteria and yeast and other fungal organisms. In surgical procedures that require cutting of bone, such as orthopedic surgeries, such bacteria include microbial organisms that are associated with an orthopedic device or may be otherwise present at the site of the device, including tissues such as skin, blood, muscle, cartilage, and bone. Thus, any organism that has the potential to enter surreptitiously and colonize at a bone defect or area of orthopedic repair and trauma may be targeted in accordance with the present technology. In particular, organisms that colonize the skin of the subject are targeted, since these organisms may enter the subject at the site where the orthopedic implant was inserted.

Particularly relevant target organisms include Gram-positive and Gram-negative bacteria, and yeasts. Such organisms include *Klebsiella, Enterobacter, Acinetobacter, Pseudomonas, Escherichia*, and *Staphylococcus*. Specific bacteria include *Staphylococcus aureus*, as represented by strain NCTC 8325 and methicillin resistant strains which presently cause significant problems in hospital environments. Further targets are *Staphylococcus epidermidis*, represented by strain NCTC 11047, *Coryneforms* and *Diptheroids*, for example, *Corynebacteria diptheriae* represented by strain NCTC 5002 and *C. xerosis* represented by strain ATTC 7711, and yeasts such as *Candida albicans*, represented by strain ATCC 26555.

Anti-infective agents useful in the compositions of the present technology include any compound that has inhibitory activity against the growth of microbes (e.g., such as bacteria and yeast), preferably bacteria as discussed above. Preferably, the anti-infective agent is selected from the group consisting of antibiotics, antimicrobial peptides, antimicrobial peptide mimetics, disinfectants, antiseptics, antimicrobial metal ions, including salts and nanoparticles of silver and copper, sugar alcohols, such as xylitol and erythritol, essential oils, salicylic acid, methyl salicylate, and mixtures thereof. The amount of antimicrobial agent in the phospholipid compositions may range from about 0.1% to about 20%, from about 1% to about 15%, from about 1% to about 10%, or from about 1% to about 5% of the composition.

Suitable antimicrobial agents may have at least one or more of the following properties: 1) the ability to prevent growth and/or replication and/or to kill pathogens which become associated with the bone defect through their ability to bind to blood, muscle and osseous tissue; 2) possessing an acceptable side effect profile, including low toxicity and allergenicity for the intended human or animal subject to be treated; 3) acceptable efficacy at the site of the bone defect, with limited development of microbial resistance; 4) acceptable miscibility or solubility with the phospholipid; and 5) stability in the phospholipid when applied to a bone to stop bleeding.

Antibiotics useful herein include, for example, rifamycins, fosfobycin, fusidic acid, glycylcyclines, aminoglycosides, quinolones, glycopeptides, bismuth thiols, sulfonamides, trimethoprim, macrolides, oxazolidinones, β-lactams, lincosamides, chloramphenicol, gramicidins, polymyxins, lipodepsipeptides, bacitracins, tetracyclines, penicillin, ampicillin, cefazolin, clindamycin, erythromycins, levofloxacin, vancomycin, and mixtures thereof. In various embodiments, the anti-infective comprises rifampin and a second anti-infective, such as a combination of rifampin and a minocycline.

Tetracycline antibiotics refer to a number of antibiotics of either natural, or semi-synthetic origin, derived from a system of four linearly annealed six-membered rings (1,4,4a,5,5a,6,11,12a-octahydronaphthacene) with a characteristic arrangement of double bonds. The tetracycline antibiotic can include one or more tetracyclines, and/or semi-synthetic tetracyclines such as doxycycline, oxytetracycline, demeclocycline, lymecycline, chlortetracycline, tigecycline and minocycline. A preferred tetracycline is minocycline or minocycline hydrochloride. The amount of tetracycline present in the phospholipid composition can range from about 5 µg/cm$^2$ to about 1000 µg/cm$^2$, or from about 10 µg/cm$^2$ to about 800 µg/cm$^2$.

Rifamycin class of antibiotics is a subclass of antibiotics from the ansamycin family of antibiotics. The present antibiotic agent or agents can include one or more rifamycin antibiotics from the group rifamycin B, rifampin or rifampicin, rifabutin, rifapentine and rifaximin. Rifampin is commercially available as Rifadin and Rimactane from Sanofi-Aventis U.S. LLC. (Bridgewater, N.J., USA).

Antimicrobial peptides useful herein include, for example, host defense proteins, defensins, magainins, cathetlicidins, protegrins, lantibiotics, nisins, and synthetic mimics of host defense proteins such as cationic steroids. Antiseptics and disinfectants include, for example, chlorhexidine, polyhexanide, triclosan, and iodine-delivering formulas such as betadine or povidone-iodine. Metal ions include various formulations of silver that effectively release silver ions, including silver salts and silver nanoparticles, or copper salts and copper nanoparticles that release copper ions.

Food preservatives that would effectively inhibit microbial attachment or growth include, for example, epsilon polylysine, nisin, and various essential oils including oils from cinnamon, thyme, clove, lemon, lime, orange, and geranium or purified active anti-infective ingredients from essential oils such as cinnamaldehyde, garnesol, carvacrol, and thymol.

Several other anti-infective agents and/or additives can be included in various embodiments. Salicylic acid and its metabolite methyl salicylate have anti-infective properties and could be additives to hemostatic phospholipids. Sugar alcohols and polyols, such as xylitol and erythritol, could be additives to the phospholipids. Such sugar alcohols can have anti-infective properties by preventing bacterial adhesion or bacterial biofilm formation. Some polysaccharides, such as chitosan and alginate, have some anti-infective properties and could be used as additives. Other polysaccharides, such as carboxymethylcellulose, can be added to improve handling or physical properties. Antioxidants that could be used as additives include vitamins E and/or C (as tocopherol acetate and ascorbic acid for instance). Other additives include small molecule drugs, such as anesthetics, including bupivacaine, to manage pain, or small molecules that could increase bone repair, such as bisphosphonates, or insulin mimetics, such as vanadium compounds, including vanadyl acetylacetonate. Other additives include growth factors or cytokines to modulate the repair and inflammatory processes.

The hemostatic compositions of the present technology can be made by cold molding a phospholipid, such as phosphatidylcholine, into a stick shape, packaging the stick-shaped phospholipid, and sterilizing the stick-shaped phospholipid with 25-40 kGy of gamma radiation or by electron beam radiation. Alternatively, hemostatic compositions can be made by aseptic methods.

In various embodiments, compositions may be made using compounding extruders, such as co-rotating twin screw extruders, to mix two or more materials. Additives such as antibiotics, antioxidants, etc. can be added to a hopper either as powders or premixed as a slurry or solution with the phospholipid. Mixed and extruded formulations can be cold pressed, or pressed with mild heat, into a desired shape, for insertion into packaging. If natural phosphatidylcholine or hydrogenated phosphatidylcholine is used, heat is preferably limited to mild temperatures because phospholipids are subject to thermal degradation, and so cannot be melted and then cooled in a mold or applicator.

In various embodiments, a hemostatic composition is produced by positioning a phospholipid into a mortar and optionally transferring at least one anti-infective agent into the mortar as well. Optionally, the mortar is heated from about 30° C. to about 80° C. Preferably, when heated, the mortar is heated to about 40° C. In a preferred embodiment, the phospholipid is phosphatidylcholine. In a more preferred embodiment, the phospholipid is Phospholipon® 90G. The optional at least one anti-infective agent can be a powder or a powder dissolved in a biocompatible solvent. The phospholipid and optional at least one anti-infective agent are then mixed by grinding with a pestle to form a mixture. After grinding, the mixture is repeatedly folding by kneading until a smooth, uniform, waxy solid hemostatic composition is generated. The hemostatic composition can be shaped, for example as a stick, by cold molding. After molding, the hemostatic composition can be packaged and sterilized. Sterilizing can be achieved by 25-40 kGy of gamma radiation or by electron beam radiation.

Alternatively, the phospholipid and the optional additives can be mixed by first dissolving in organic solvents to form true solutions, then mixing the solutions together. The solvents are then removed to leave a completely homogenous phospholipid-based solid formulation that can be cold molded into shapes for insertion into an applicator. The solvent removal can be accomplished by either freeze-drying or by spray-drying. For freeze-drying, the equipment and the solvent are selected, so that the eutectic point, or the transition from frozen to sublimation, and therefore the shelf temperature to maintain in the drying phase, is feasible and also that a condenser temperature can be achieved to pull the solvent out of the exhaust. The vacuum pump is preferably explosion proof. The solvent may alternatively be a mixture comprising organic solvent and water. Non-limiting examples of appropriate solvents include tertiary butanol, ethanol, isopropanol, acetonitrile and methanol. A method of removing the organic solvent comprises a spray-drying operation in which a solution comprising lipid carrier and additives in organic solvent is atomized (for example by pressure or ultrasonic) into the top of a tall drying chamber.

Very dry gas (compressed nitrogen, air, or argon for example) can also be introduced into the top of the chamber. The solvent evaporates into the gas as atomized droplets fall to the bottom of the chamber. The product is collected in the bottom of the chamber and can be removed and cold molded into an appropriate shape before insertion in the applicator. The gas phase is exhausted at the bottom of the chamber as well and sent through a condenser or chiller to remove the solvent for reuse or disposal. Non-limiting examples of solvents used in spray drying operations include methanol, ethanol, toluene, hexane, acetone, ethylacetate, and dichloromethane.

Solvent-based processing can be advantageous if the phospholipid contains saturated lipids that are normally a powdery solid and that need to be blended with unsaturated or small chain lipids that are liquid at room temperature in order to achieve a waxy texture that will perform well as a hemostatic agent. Saturated lipids that are normally a powder and need such modification include hydrogenated phospholipids and fully saturated triacylglycerols such as trimyristate, tristearate, or tripalmitate. Such saturated lipids can be fully mixed with either unsaturated and/or short chain lipids such as unsaturated medium-chain triacylglycerols from corn oil, olive oil, palm oil, sunflower oil, or rapeseed oil for instance, or unsaturated simple fatty acids (oleic acid, linoleic acid). The solvent based process will facilitate the mixing of these types of lipid components.

After packaging the hemostatic composition, it may be terminally sterilized by gamma irradiation or by electron beam sterilization. Alternatively, the composition may be prepared and packaged by aseptic processing.

The present technology also provides methods for achieving hemostasis in bleeding bone by use of hemostatic compositions. The method comprises administering a safe and effective amount of a phospholipid composition to a location of bleeding on a bone in a mammalian subject. The mammalian subject can be a human or a nonhuman. A preferred phospholipid is phosphatidylcholine. More preferably, the phosphatidylcholine is Phospholipon® 90G from Lipoid (Koln, Germany). Unlike BoneWax, the hemostatic composition is resorbable, biodegradable, and biocompatible. Furthermore, the cost of producing the hemostatic composition is competitive with the cost of producing beeswax products. A bleeding bone can result from surgery such as orthopedic surgery or a sternotomy. In various embodiments, the hemostatic composition comprises at least one anti-infective agent. Suitable anti-infective agents are discussed above; however, in a preferred embodiment, the at least one anti-infective agent comprises rifampin and minocycline. Administering the phospholipid hemostatic composition can performed by mechanical tamponade. In various embodiments, the hemostatic composition consists, or consists essentially, of a phosphatidylcholine and optionally at least one anti-infective agent.

The materials and processes of the present technology are illustrated in the following non-limiting example.

EXAMPLE 1

Sample Preparation

A preparation comprising about 94% soy derived phosphatidylcholine (Phospholipon® 90G, Lipoid, Köln, Germany) is compressed and cold-molded into a 2.5 gram rectangular shape roughly about 1 cm wide, 3 cm long, and 3 mm deep. Phospholipon® 90G is a minimum of 94% by weight purified phosphatidylcholine, with the balance primarily lysophosphatidylcholine and other nonpolar lipids. Phospholipon® 90G is a slightly yellow, waxy solid. The 2.5 gram molded samples are packaged in foil pouches and sterilized with a standard gamma radiation cycle (2.5 to 4/0 kGy).

Hemostasis Testing

Hemostatic properties of the phosphatidylcholine, when applied to cortical bone defects on the rib in a swine model, are evaluated. The results achieved by phosphatidylcholine are compared to commercially available bone hemostats, Ostene® (Ceremed, Los Angeles, Calif.) and BoneWax (Ethicon, Somerville, N.J.).

One pig had a skin incision approximately 12 cm long made over the middle of a selected rib. The muscle and soft tissue are reflected. Electro-cautery is utilized to control bleeding of the cut muscle and soft tissues. Within the exposed rib area, three square defects are created in the cortical surface of the rib. The defects measure approximately 1 cm×1.5 cm. Cortical bone was removed from the defect sites until widespread punctate bleeding to brisk oozing occurred. Presence of bleeding is noted as "slow oozing" or "brisk bleeding". Each of the three defects is created prior to beginning the treatment of any of the three defects at the rib. The three defects per rib are treated with phosphostidylcholine, Ostene, or BoneWax. The presence of or absence of bleeding are recorded immediately following completion of application, and at 5 minute intervals after placement of articles in the defect. If bleeding is still present at 15 minutes following treatment, the treatment is considered unsuccessful at the site. Bleeding reoccurring after hemostasis is achieved is recorded. Once the three defects at one rib are all treated, another rib is exposed and defects similarly created and treated. The treatments are alternated between treatment location, i.e., dorsal, middle, or ventral defect to avoid any location bias. Six defects on six ribs are treated with each test article. Following completion of the procedure, the animal is euthanized.

Handling Observations

The phosphatidylcholine is easily workable, slightly oily when softened, and easy to apply to the defect sites. The phosphatidylcholine, and comparative products Ostene and BoneWax, handle similarly during application. Ostene is easily workable, but not cohesive until material is softened with manipulation. It is easy to apply to the defect sites. BoneWax is easily workable, softened with manipulation and easy to apply to the defect sites.

Bleeding Observations

Similar bleeding is noted for all sites following creation with all sites considered to have slow oozing. The results are shown in Table 1 as a chart and graphically in FIG. 1. Following treatment, hemostasis is achieved immediately after application with all sites with each article. However, over course of the 15 minute observation period, bleeding returns with all articles. Although not statistically significant, the BoneWax had the highest incidence of hemostasis, followed by phosphatidylcholine, and then the Ostene. In general, when bleeding is noted, it starts at focal sites. Both for the phosphatidylcholine and comparison products, bleeding progresses as time goes on and became more brisk. Both the phosphatidylcholine and Ostene soften at the application site to the point of a "melting" appearance. Bleeding for the BoneWax tends to stay more focal, and does not progress in severity. Under the conditions of the study, no statistical differences in hemostasis are noted between compositions.

TABLE 1

Absence or Presence of Bleeding after 5, 10, and 15 minutes of hemostatic composition administration.

| Rib Number | Defect | Pretreatment Bleeding | Treatment | Presence or Absence of Bleeding (following bleeding) | | | |
|---|---|---|---|---|---|---|---|
| | | | | Immediately | 5 minutes | 10 minutes | 15 minutes |
| 1 | Dorsal | Slow oozing | Phosphatidylcholine | Absent | Absent | Absent | [b] |
| | Middle | Slow oozing | Ostene | Absent | Absent | Oozing | Bleeding |
| | Ventral | Slow oozing | BoneWax | Absent | Absent | Absent | Absent |
| 2 | Dorsal | Slow oozing | Ostene | Absent | Oozing | Bleeding | Bleeding |
| | Middle | Slow oozing | BoneWax | Absent | Absent | Bleeding | Bleeding |
| | Ventral | Slow oozing | Phosphatidylcholine | Absent | [a] | Bleeding | Bleeding |
| 3 | Dorsal | Slow oozing | BoneWax | Absent | Absent | Absent | Absent |
| | Middle | Slow oozing | Phosphatidylcholine | Absent | Bleeding | Bleeding | Bleeding |
| | Ventral | Slow oozing | Ostene | Absent | Bleeding | Bleeding | Bleeding |
| 4 | Dorsal | Slow oozing | Phosphatidylcholine | Absent | Bleeding | Bleeding | Bleeding |
| | Middle | Slow oozing | Ostene | Absent | Absent | Bleeding | Bleeding |
| | Ventral | Slow oozing | BoneWax | Absent | Absent | Bleeding | Bleeding[c] |
| 5 | Dorsal | Slow oozing | Ostene | Absent | Bleeding | Bleeding | Bleeding |
| | Middle | Slow oozing | BoneWax | Absent | Absent | Bleeding | Absent |
| | Ventral | Slow oozing | Phosphatidylcholine | Absent | Absent | Bleeding | Bleeding |
| 6 | Dorsal | Slow oozing | BoneWax | Absent | Bleeding | Bleeding | Not needed |
| | Middle | Slow oozing | Phosphatidylcholine | Absent | Bleeding | Bleeding | Not needed |
| | Ventral | Slow oozing | Ostene | Absent | Bleeding | Bleeding | Not needed |

The embodiments and the examples described herein are exemplary and not intended to be limiting in describing the full scope of compositions and methods of the present technology. Equivalent changes, modifications and variations of embodiments, materials, compositions and methods can be made within the scope of the present technology, with substantially similar results.

Non-Limiting Discussion of Terminology

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting ingredients, components or process steps, Applicants specifically envision embodiments consisting of, or consisting essentially of, such ingredients, components or processes excluding additional ingredients, components or processes (for consisting of) and excluding additional ingredients, components or processes affecting the novel properties of the embodiment (for consisting essentially of), even though such additional ingredients, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein

What is claimed is:

1. A method for achieving hemostasis comprising, administering to a site of bleeding in a bone a solid phospholipid composition comprising phosphatidylcholine and, optionally, tocopherol, wherein the composition is effective to achieve hemostasis at the site of bleeding in the absence of further hemostatic agents.

2. The method according to claim 1, wherein the phospholipid composition further comprises lysophosphatidylcholine.

3. The method according to claim 1, wherein the composition further comprises a substance to manage pain, salicylic acid, an antioxidant, a bisphosphonate, a growth factor, a cytokine to modulate inflammation or tissue repair, or a combination thereof.

4. The method according to claim 1, wherein the composition further comprises an anti-infective polysaccharide, an anti-infective essential oil, an anti-infective sugar alcohol, an antibiotic, an antimicrobial peptide, a synthetic mimic of an antimicrobial peptide, a disinfectant, an antiseptic, an antimicrobial metal ion, or a combination thereof.

5. The method according to claim 1, wherein the composition is malleable.

6. The method according to claim 1, wherein the phospholipid comprises phosphatidylcholine derived from a natural source and synthetic phosphatidylcholine.

7. The method according to claim 1, wherein administering comprises mechanical tamponade.

8. The method according to claim 1, wherein the phospholipid comprises phosphatidylcholine that is fully saturated.

9. The method according to claim 1, wherein the composition further comprises tocopherol.

10. The method according to claim 1, wherein the phospholipid comprises phosphatidylcholine that is fully saturated, and phosphatidylcholine that is unsaturated.

11. The method according to claim 1, wherein the composition has a putty consistency or a waxy consistency.

12. A method for achieving hemostasis comprising, mechanical tamponade at a site of bleeding in a bone using a solid composition comprising phosphatidylcholine and, optionally, tocopherol, and, optionally, an anti-infective agent, and wherein the solid composition is effective to achieve mechanical tamponade hemostasis without the use of another hemostatic agent.

13. The method according to claim 12, wherein the solid composition further comprises lysophosphatidylcholine and tocopherol.

14. The method according to claim 12, wherein the composition further comprises a substance to manage pain, salicylic acid, an antioxidant, a bisphosphonate, a growth factor, a cytokine to modulate inflammation or tissue repair, or a combination thereof.

15. A method for achieving hemostasis of a bleeding bone in a mammalian subject comprising administering to the site of the bleeding a composition consisting of phosphatidylcholine and, optionally, a tocopherol.

16. The method according to claim 15, wherein the phosphatidylcholine comprises saturated phosphatidylcholine and unsaturated phosphatidylcholine.

17. The method according to claim 1, wherein the phospholipid comprises saturated phospholipid or partially saturated phospholipid, and unsaturated phospholipid.

18. The method according to claim 12, wherein the phosphatidylcholine is derived entirely from a natural source, is synthetic phosphatidylcholine, or a combination of natural phosphatidylcholine and synthetic phosphatidylcholine.

\* \* \* \* \*